United States Patent [19]

Sundeen et al.

[11] 4,288,456
[45] Sep. 8, 1981

[54] COMPOSITIONS CONTAINING 1-ARYL-5-(2-PROPENYLAMINO)-1-PENTEN-3-ONES AND METHOD FOR TREATING INFLAMMATORY CONDITIONS

[75] Inventors: Joseph E. Sundeen, Yardley, Pa.; Tamara Dejneka, Skillman; Frederic P. Hauck, Bridgewater, both of N.J.

[73] Assignee: E. R. Squibb & Sons, Inc., Princeton, N.J.

[21] Appl. No.: 188,647

[22] Filed: Sep. 19, 1980

[51] Int. Cl.$^3$ ............................................. A61K 31/135
[52] U.S. Cl. ..................................................... 424/330
[58] Field of Search ......................................... 424/330

[56] References Cited

U.S. PATENT DOCUMENTS 3,094,561 6/1963 Faust et al. ........................ 260/567.6
4,173,649 11/1979 Sundeen et al. ....................... 424/304

OTHER PUBLICATIONS

Dimmock et al., J. Pharmaceutical Sciences 65, 482 (1976).

Dimmock et al., J. Pharmaceutical Sciences 65, 69 (1974).

Gschwend et al., J. Org. Chem. 38, 2169 (1973).

*Primary Examiner*—Stanley J. Friedman
*Attorney, Agent, or Firm*—Lawrence S. Levinson; Burton Rodney

[57] ABSTRACT

Pharmaceutical compositions containing 1-aryl-5-(2-propenylamino)-1-penten-3-ones and salts thereof having the structure

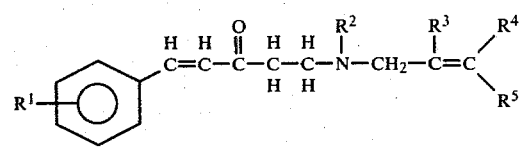

wherein $R^1$ is hydrogen, lower alkyl, lower alkoxy, halogen, hydroxy, lower alkanoyloxy, nitro, cyano, amino, carboxy or lower alkoxycarbonyl, and $R^2$, $R^3$, $R^4$ and $R^5$ are the same or different and are hydrogen or lower alkyl. These compositions are useful in treating inflammatory conditions.

8 Claims, No Drawings

COMPOSITIONS CONTAINING 1-ARYL-5-(2-PROPENYLAMINO)-1-PENTEN-3-ONES AND METHOD FOR TREATING INFLAMMATORY CONDITIONS

BACKGROUND OF THE INVENTION

Dimmock et al. J. Pharmaceutical Sciences 65, 482 (1976) and 65, 69 (1974) disclose 5-dimethylamino-1-phenyl-1penten-3-ones of the structure

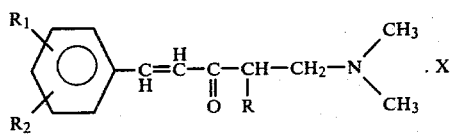

wherein $R_1$ and $R_2$ are H, or Cl, X is HCl or $CH_3I$ and R is H, $CH_3$ of $(CH_2)_4CH_3$ as inhibitors of mitochondrial function in yeast and inhibitors of blood platelet aggregation and as possessing antitumor properties.

Gschwend et al, J. Org. Chem. 38, 2169 (1973) in a paper entitled "Rates of Intromolecular Diels-Alder Reactions of Pentadienylacrylamides" disclose the synthesis of 4,5-diphenyl-2,4-pentadienylamines of the structure

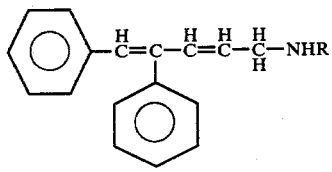

wherein R is H, $CH_3$, $C_2H_5$, i-$C_3H_7$ or t-$C_4H_9$ as well as N-alkyl-N-methyl-4,5-diphenyl-2,4-pentadienylamine.

U.S. Pat. No. 3,094,561 to Faust et al discloses compounds of the structure

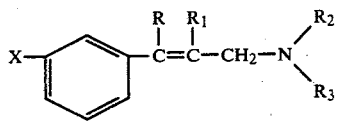

wherein X is $Cl_n$ or $Br_n$, n is 1 or 2, R and $R_1$ each represent H or lower alkyl, and $R_2$ and $R_3$ each represent H, lower alkyl, lower alkenyl or lower alkanol, which are said to possess pressor activity, that is, blood pressure raising activity.

U.S. Pat. No. 4,173,649 to Sundeen et al discloses 5-phenyl-2,4-pentadien-1-amines and salts thereof having the structure

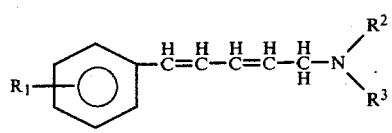

wherein $R^1$ is hydrogen, lower alkyl, lower alkoxy, hydroxy, lower alkanoyloxy, nitro, cyano, amino, carboxy or lower alkoxycarbonyl, and $R^2$ and $R^3$ are the same or different and are hydrogen, lower alkyl, alkenyl-lower alkyl, aralkyl, and substituted lower alkyl. These compounds are said to possess useful pharmaceutical activities due to their ability to inhibit the prostaglandin-inactivating enzyme 15-α-hydroxyprostaglandin dehydrogenase.

5-Amino-1-phenyl-1-penten-3-ones of the structure

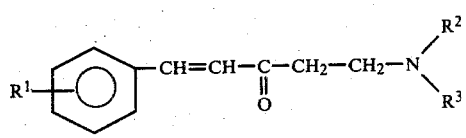

for example, 1-(2-chlorophenyl)-5-(methyl-2-propenylamino)-1-penten-3-one, hydrochloride, are disclosed as intermediates.

DESCRIPTION OF THE INVENTION

The present invention relates to antiinflammatory compositions containing 1-aryl-5-(2-propenylamino)-1-penten-3-ones and to a method of employing such compounds in treating antiinflammatory conditions.

The 1-aryl-5-(2-propenylamino)-1-penten-3-ones present in the compositions of the invention have the following structure

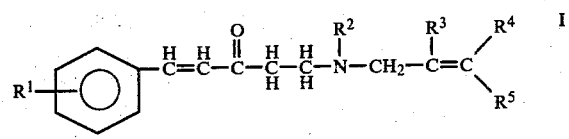

wherein $R^1$ is hydrogen, lower alkyl, lower alkoxy, halogen, hydroxy, lower alkanoyloxy, nitro, cyano, amino, carboxy or lower alkoxycarbonyl, and $R^1$, $R^2$, $R^3$ and $R^4$ may be the same or different and are hydrogen or lower alkyl, and physiologically acceptable salts thereof.

Preferred are those compounds of formula I wherein $R^1$ is hydrogen or halogen, for example 2-Cl, $R^2$ is methyl or ethyl and $R^3$, $R^4$ and $R^5$ are each hydrogen.

Unless otherwise indicated, the term "lower alkyl" or "alkyl" as employed herein includes both straight and branched chain radicals of up to eight carbon atoms, for instance, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, and the like.

Unless otherwise indicated, the term "lower alkoxy or "alkoxy" includes straight and branched chain radicals which correspond to the above lower alkyl groups attached to an oxygen atom.

Unless otherwise indicated, the term "lower alkanoyloxy" as employed herein includes any of the above lower alkyl groups linked to a

group.

The compounds of formula I of the invention are prepared by the Mannich reaction between a 4-phenyl-3-butene-2-one of the structure

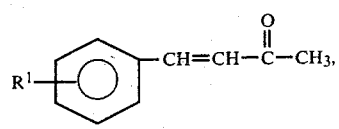

an amine of the structure

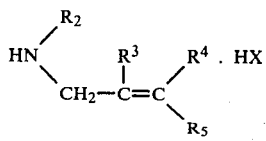

wherein X is Cl or Br, and paraformaldehyde under reflux and in the presence of an anhydrous alcohol in accordance with the procedure outlined in Dimmock et al, J. Pharmaceutical Science, 63, 69 (1974) and 65, 482 (1976), to form the compounds (I) of the invention.

Depending on the reaction conditions and the starting materials used, the compounds of formula I are obtained in the free form or in the form of their acid-addition salts. The salts thereof can be converted into the free compounds in a known manner such as by reaction with a basic agent. Free bases which may be obtained can be converted into pharmaceutically acceptable acid-addition salts by reaction with a variety of acids. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids, such as maleic, fumaric, tartaric, citric, acetic, benzoic, 2-acetoxybenzoic, salicyclic, succinic, nicotinic, methanesulfonic or cyclohexanesulfamic.

The compounds of formula I have antiinflammatory activity as measured by the mouse active arthus (MAA) test and/or other related tests and are useful as antiinflammatory agents and may be used, for example, in a manner similar to phenylbutazone or indomethacin. They may be used to decrease joint swelling, tenderness, pain and stiffness in mammalian species, e.g., in conditions, such as rheumatoid arthritis. The quantity administered ranges from about 1 mg to about 150 mg per kg and preferably from about 5 mg to about 75 mg per kg of body weight per day.

A compound of formula I can be administered orally or parenterally (for example, intraperitoneally, subcutaneously, intramuscularly or intravenously). Powders can be prepared by comminuting the active ingredient with a similarly comminuted diluent, such as starch or lactose. Suitable forms of oral administration include capsules, tablets, troches, elixirs, wafer, chewing gum, syrups, and a suitable form for parenteral administration in a sterile injectable. Such unit dosage forms are prepared by compounding with a conventional vehicle, excipients, binders, preservatives, stabilizers, flavoring agents or the like as called for by acceptable pharmaceutical practice. Also, the compounds used in this invention can be formulated with other pharmaceutically active compounds.

The tablets, troches, pills, capsules and the like may also contain the following: a binder, such as gum tragacanth, acacia, corn starch or gelatin; an excipient, such as dicalcium phosphate, a disintegrating agent, such as corn starch, potato starch, alginic acid and the like; a lubricant, such as magnesium stearate; and a sweetening agent, such as sucrose, lactose or saccharin may be added or a flavoring agent such as peppermint, oil of wintergreen or cherry flavoring. When the dosage unit form is a capsule, it may contain in addition to materials of the above type a liquid carrier, such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring, such as cherry or orange flavor. Of course, any material used in preparing any dosage unit form should be pharmaceutically pure and substantially non-toxic in the amounts employed.

The following examples are illustrative of the invention and represent preferred embodiments. Other modifications may be readily produced by suitable variations of the reactions. All temperatures are on the Centrigrade scale.

EXAMPLE 1

1-(2-Chlorophenyl)-5-(methyl-2-propenylamino)-1-penten-3-one, hydrochloride (1:1)

A. N-methyl-allylamine (JCS, 1479(1950))

Benzaldehyde (89 g, 0.8 mole) is cooled in ice while treating with 46 g (0.8 mole) of allylamine. The mixture is allowed to warm to 25° C., ether (300 ml) is added and the water separated. Benzene (1 l.) is added, the cloudy mixture dried (Nahd 2SO4) and evaporated to 600 ml. To this clear benzene solution is added 150 g (1.05 mole) of methyliodide and the mixture heated under slight pressure for 14 hours. Cooling and swirling gives a mass of solid which is filtered and washed with benzene. The solid is treated with warm water and the aqueous extracted with ether. The clear aqueous layer is basified with 50% NaOH and saturated with Na2CO3. The liberated base is extracted with ether, dried (Na2CO3), and distilled at 1 atm. The fraction boiling at 36° C. is discarded. The fraction with bp=37°-60° is treated with excess HCl in isopropanol, stripped to an oil, toluene added and evaporated to 8.5 g of a foam (0.08 mole). At 62°-64° a sample of pure amine is collected, 6 g (0.085 mole), for a total of 0.165 mole (20%) of amine.

B. 1-(2-Chlorophenyl)-5-(methyl-2-propenylamino)-1-penten-3-one, hydrochloride (1:1)

The 6 g sample of free base (of Part A) is converted to hydrochloride, combined with the other sample of hydrochloride, and heated with paraformaldehyde (9.8 g, 0.33 mole) and 4-(2-chlorophenyl)-3-buten-2-one (29 g, 0.16 mole) in 300 ml of absolute ethanol for 2½ hours. The clear solution is evaporated and dissolved in 300 ml of ethyl acetate. A sample of this solution is diluted with ether and scratched. The resulting solid is used to seed the ethyl acetate solution. The solid which crystallizes is filtered and dried in vacuo to give 32 g (66%) of Mannich base hydrochloride.

A 4 g sample is recrystallized twice from ether-acetonitrile to give 1.3 g of white solid, m.p. 136°-140° C.

EXAMPLES 2 TO 20

Following the procedure of Example 1 except substituting for trans-4-phenyl-3-butene-2-one, the compound shown in Column I of Table I below, and substituting for allylamine, the amine shown in Column II, the product shown in Column III is obtained.

TABLE I

| | Column I | | | | Column II | | | | Column III |
|---|---|---|---|---|---|---|---|---|---|
| Ex. No. | $R^1$(position) | $R^2$ | $R^3$ | $R^4$ | $R^5$ | $R^1$ | $R^2$ $R^3$ $R^4$ $R^5$ | | |
| 2. | H | H | $C_2H_5$ | H | $C_2H_5$ | | | | |
| 3. | $CH_3$(2) | H | H | $CH_3$ | H | as in Column I | as in Column II | | |
| 4. | $C_2H_5$(4) | $CH_3$ | H | H | $C_3H_7$ | | | | |
| 5. | $CH_3O$(2) | H | $C_2H_5$ | H | $CH_3$ | | | | |
| 6. | $C_2H_5O$(3) | H | $CH_3$ | H | $CH_3$ | | | | |
| 7. | OH(2) | H | H | H | $CH_3$ | | | | |
| 8. | OH(4) | H | $CH_3$ | H | $C_3H_7$ | | | | |
| 9. | $CH_3CO$(2) (with =O) | H | $C_2H_5$ | H | $C_2H_5$ | | | | |
| 10. | Br(4) | $C_2H_5$ | H | H | $CH_3$ | | | | |
| 11. | Cl(3) | $CH_3$ | H | $CH_3$ | —$CH_3$ | | | | |
| 12. | $NO_2$(2) | $CH_3$ | H | $CH_3$ | H | | | | |
| 13. | CN(2) | H | H | H | $C_2H_5$ | | | | |
| 14. | CN(4) | $CH_3$ | H | $CH_3$ | H | | | | |
| 15. | $NH_2$(2) | $C_2H_5$ | $CH_3$ | $C_2H_5$ | $CH_3$ | | | | |
| 16. | $NH_2$(4) | H | $CH_3$ | H | $C_2H_5$ | | | | |
| 17. | COOH(2) | H | $CH_3$ | H | $CH_3$ | | | | |
| 18. | COOH(4) | $CH_3$ | H | $CH_3$ | $C_2H_5$ | | | | |
| 19. | $CH_3OC$(2) (with =O) | $C_2H_5$ | $C_2H_5$ | $CH_3$ | $CH_3$ | | | | |
| 20. | $C_2H_5OC$(4) (with =O) | H | $CH_3$ | H | H | | | | |

EXAMPLE 21

Parenteral Composition Containing 1-(2-Chlorophenyl)-5-(methyl-2-propenylamino)-1-penten-3-one Hydrochloride A dispersion suitable for parenteral administration is prepared by dispersing 1 g of 1-(2-chlorophenyl)-5-(methyl-2-propenylamino)-1-penten-3-one, hydrochloride in about 100 ml of water for injection.

EXAMPLE 22

Tablets Containing 1-(2-Chlorophenyl)-5-(methyl-2-propenylamino)-1-penten-3-one Hydrochloride The following ingredients are used to make 1,000 200 mg tablets each containing 100 mg of active ingredient:

| | | |
|---|---|---|
| 1-(2-Chlorophenyl)-5-(methyl-2-propenylamino)-1-penten-3-one, hydrochloride | 100 | gm |
| Polyvinyl pyrrolidone | 7.5 | gm |
| Lactose | 20 | gm |
| Magnesium stearate | 3.5 | gm |
| Corn starch | 17.5 | gm |
| Avicel (microcrystalline cellulose) | 51.5 | gm |

The medicament and lactose are thoroughly admixed, the polyvinyl pyrrolidone is dissolved in ethanol USP to make a 30% solution. This solution is used to granulate the mixture of medicament and lactose. The granulation is passed through a No. 16 screen and air dried. The dried granulation is then passed through a No. 20 screen. To the screened granulate are added the magnesium stearate, Avicel and the corn starch and the mixture is blended. The blend is then compressed into 200 mg tablets on a standard concave punch. The tablets are then veneer coated with methyl cellulose in a spray gun.

What is claimed is:

1. The method of treating an inflammatory condition in a mammalian species, which comprises administering to said specie a composition comprising a therapeutically effective amount of a compound of the structure

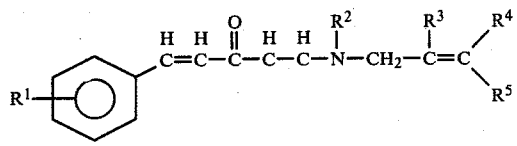

wherein $R^1$ is hydrogen, lower alkyl, lower alkoxy, halogen, hydroxy, nitro or amino, and $R^2$, $R^3$, $R^4$ and $R^5$ may be the same or different and are hydrogen or lower alkyl, and physiologically acceptable salts thereof, and a pharmaceutically acceptable carrier therefor.

2. The method as defined in claim 1, wherein said inflammatory condition is arthritis.

3. The method as defined in claim 1 wherein $R^1$ in said compound is halogen or hydrogen.

4. The method as defined in claim 1 wherein $R^1$ in said compound is Cl.

5. The method as defined in claim 1 wherein $R^1$ in said compound is 2-Cl.

6. The method as defined in claim 5 wherein $R^2$ in said compound is lower alkyl.

7. The method as defined in claim 6 wherein $R^3$, $R^4$ and $R^5$ in said compound are hydrogen.

8. The method as defined in claim 5 wherein said compound has the name 1-(2-chlorophenyl)-5-(methyl-2-propenylamino)-1-penten-3-one, hydrochloride.

* * * * *

UNITED STATES PATENT AND TRADEMARK OFFICE
CERTIFICATE OF CORRECTION

PATENT NO. : 4,288,456

DATED : September 8, 1981

INVENTOR(S) : Joseph E. Sundeen et al.

It is certified that error appears in the above-identified patent and that said Letters Patent are hereby corrected as shown below:

Column 1, line 10, "1penten" should read --1-penten--.
Column 1, line 23, "Intromolecular" should read --Intramolecular--.
Column 4, line 28, "Nahd2SO$_4$" should read --Na$_2$SO$_4$--.

Signed and Sealed this

Eighth Day of December 1981

[SEAL]

Attest:

*Attesting Officer*

GERALD J. MOSSINGHOFF
*Commissioner of Patents and Trademarks*